Oct. 20, 1970 F. W. ANDERSON Plant Pat. 2,993
NECTARINE TREE
Filed Oct. 7, 1968
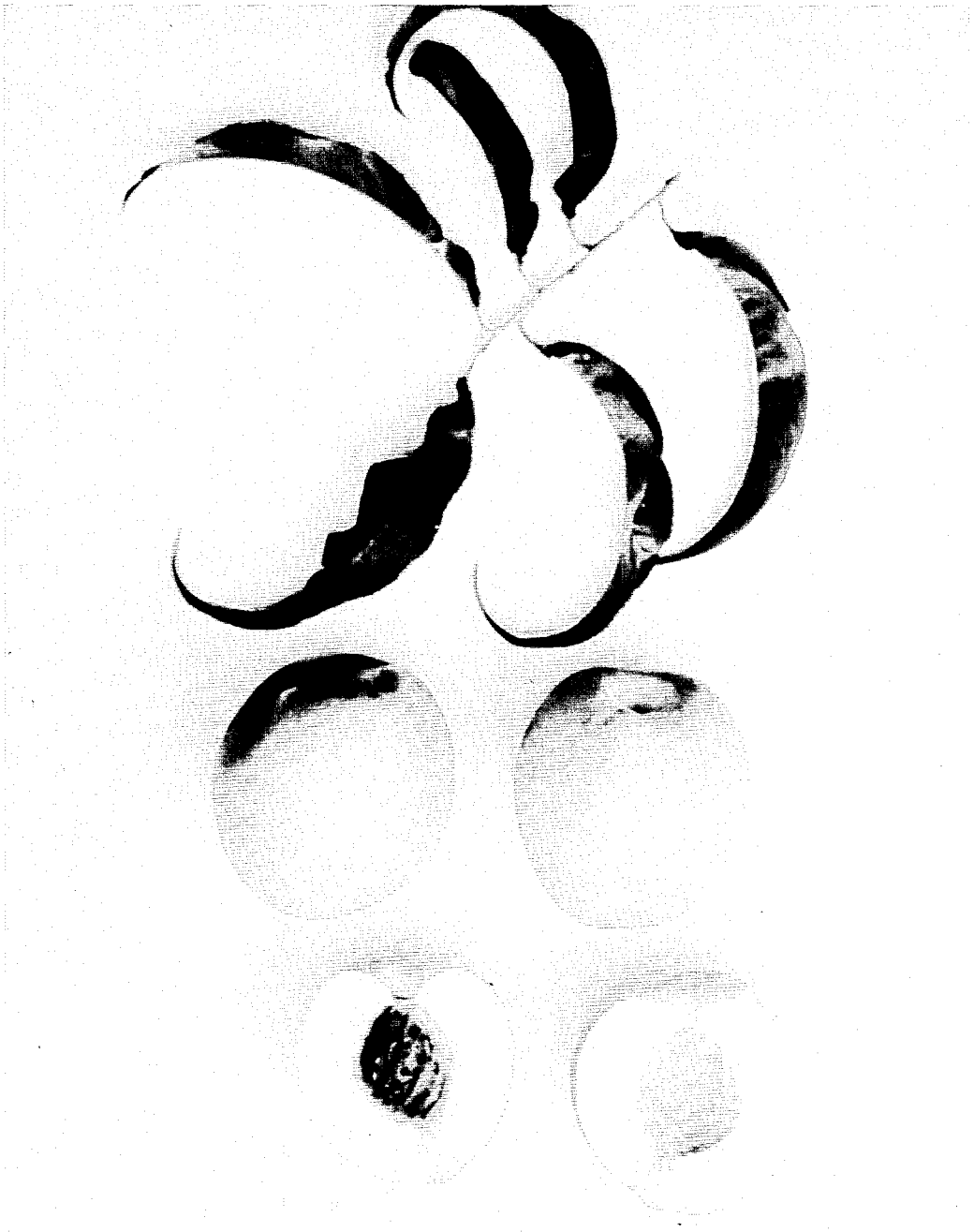
INVENTOR
Frederic W. Anderson
BY
Webster & Webster
ATTORNEYS

United States Patent Office

Plant Pat. 2,993
Patented Oct. 20, 1970

2,993

NECTARINE TREE

Frederic W. Anderson, Merced, Calif., assignor to Reedley Nursery, Inc., Reedley, Calif., a corporation of California

Filed Oct. 7, 1968, Ser. No. 765,701
Int. Cl. A01h *5/03*
U.S. Cl. Plt.—41 1 Claim

ABSTRACT OF THE DISCLOSURE

A variety of nectarine tree which is of large to medium size, vigorous and spreading in growth, and a regular and productive bearer of large, mid-season freestone fruit having firm yellow flesh flecked with red, and yellow skin substantially overspread with red.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The herein claimed new and distinct variety of nectarine tree was originated by me in my experimental orchard located as aforesaid, in the following manner:

Seeds from a cross of Red Grand (U.S. Plant Pat. No. 1,060) nectarine and Sun Glow (U.S. Plant Pat. No. 1,929) nectarine were planted and resulted in a number of seedlings which were maintained under careful and continuing observation.

When such first-generation seedlings bore fruit, one—and which is the instant variety—evidenced novel and commercially desirable characteristics, and was, therefore, selected by me for asexual reproduction, preparatory to the trade.

ASEXUAL REPRODUCTION OF THE VARIETY

Subsequent to origination and selection by me of the present variety of nectarine tree, in the manner above described, I asexually reproduced it by top-working on a mature nectarine tree in my said experimental orchard, and in maturity such reproductions ran true to the original tree in all respects.

SUMMARY OF THE VARIETY

The herein claimed variety of nectarine tree is of large to medium size, vigorous and spreading in growth, and a regular and productive bearer of large, mid-season freestone fruit having yellow flesh flecked with red, and yellow skin substantially overspread with red; the variety being particularly characterized by firm fruit of good shipping quality, by fruit having a ripening period approximately with the clingstone Le Grand (U.S. Plant Pat. No. 549) nectarine but providing at such time freestone fruit with melting flesh and hence of better eating quality, and by fruit which has smoother skin and more red exterior color.

The herein claimed variety of nectarine tree is further characterized, in comparison to the freestone Sun Grand (U.S. Plant Pat. No. 974) nectarine, by fruit having a ripening period two to three weeks later; the fruit otherwise being generally similar and on the average is as large or slightly larger.

The herein claimed variety of nectarine tree is one of a series originated by me in order to extend the shipping season of freestone nectarines beyond that of the Early Sun Grand (U.S. Plant Pat. No. 1,420) nectarine and the Sun Grand nectarine; these two varieties having heretofore been the leading freestone nectarines packed and shipped in California of recent years.

BRIEF DESCRIPTION OF THE DRAWING

The drawing is an illustration, by photographic reproduction in color, of fruit and leaves of the variety; one fruit being cut in half to expose and show the flesh, and with the stone remaining in place in one of such halves. The illustrated flesh color is somewhat lighter than the actual flesh color designated hereinafter.

DESCRIPTION OF THE VARIETY

The botanical details of this new and distinct variety of nectarine tree—with color definitions referenced to Maerz and Paul Dictionary of Color—are as follows:

Tree:
- *Size.*—Large to medium.
- *Vigor.*—Vigorous.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Smooth.

Leaves:
- *Size.*—Medium. Average length—6¼". Average width—1⅝".
- *Form.*—Lanceolate.
- *Thickness.*—Medium.
- *Texture.*—Smooth.
- *Margin.*—Crenate.
- *Petiole.*—Medium length—average ½". Medium thickness.
- *Glands.*—Number and position—usually 2 or 3 on petiole, and 2 on blade. Alternate. Medium size. Reniform.
- *Color.*—Top side—medium green (23–L–8). Underside—lighter green (22–L–6).

Flower buds:
- *Size.*—Medium.
- *Length.*—Medium.
- *Form.*—Plump.

Flowers:
- *Blooming period.*—About with Red Grand nectarine. Medium, as compared with other varieties.
- *Size.*—Large. Showy.

Fruit:
- *Maturity when described.*—Eating ripe.
- *Date of first picking.*—July 30, 1968.
- *Date of last picking.*—Aug. 9, 1968.
- *Size.*—Uniform. Large. Average diameter axially—2½". Average transversely in suture plane—2½".
- *Form.*—Uniform. Symmetrical. Globose.
- *Suture.*—Shallow. Extends from base to beyond apex, with slight depression beyond pistil point.
- *Ventral surface.*—Rounded slightly.
- *Cavity.*—Circular. Average depth—⅜". Average breadth—¾".
- *Base.*—Rounded.
- *Apex.*—Short. Depressed.

Skin:
- *Thickness.*—Medium.
- *Texture.*—Tender.
- *Tendency to crack.*—None noted.
- *Down.*—Wanting.

*Color.*—Yellow (10–L–5) substantially overspread with red (5–L–5) shading to darker red (7–L–6); the red to a substantial extent being mottled and streaked.

Flesh:

*Juice.*—Moderate. Rich.
*Texture.*—Firm. Melting.
*Fibers.*—Fine.
*Ripens.*—Evenly.
*Flavor.*—Subacid. Delicate.
*Aroma.*—Distinct.
*Eating quality.*—Good.
*Color.*—Yellow (10–K–5) flecked with red. Surface of pit cavity—Red (5–L–5).

Stone:

*Type.*—Free.
*Size.*—Medium. Average length—1½". Average breadth—1 3/16". Average thickness—⅞".
*Form.*—Oblong.
*Base.*—Oblique.
*Hilum.*—Broad.
*Sides.*—Equal.
*Ridges.*—Rounded. Interrupted.
*Ventral edge.*—Thick.
*Dorsal edge.*—Full.
*Tendency to split.*—Slight.
*Color.*—Garnet red (7–K–6).

Use: Market. Dessert. Long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is of large to medium size, vigorous and spreading in growth, and a regular and productive bearer of large freestone fruit having firm yellow flesh flecked with red, and yellow skin substantially overspread with red; the variety being particularly characterized, in comparison to the clingstone Le Grand nectarine, by approximately the same ripening period but providing at such time freestone fruit with melting flesh, and by fruit which has smoother skin and more red exterior color; and further characterized, in comparison to the freestone Sun Grand nectarine, by generally similar fruit of the same or slightly larger size but ripening two to three weeks later.

No references cited.

ROBERT E. BAGWILL, Primary Examiner